United States Patent
Maeder et al.

(10) Patent No.: US 8,343,543 B2
(45) Date of Patent: *Jan. 1, 2013

(54) LIPASE INHIBITING COMPOSITION

(75) Inventors: Karsten Maeder, Freiburg (DE); Rainer Eugen Martin, Grenzach-Wyhlen (DE); Susanne Raab, Leinfelden-Echterdingen (DE); Lukas Christoph Scheibler, Augst (CH); Thomas Schindler, Loerrach (DE); Marco Schroeder, Schopfheim (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/213,379

(22) Filed: Aug. 19, 2011

(65) Prior Publication Data

US 2011/0301231 A1 Dec. 8, 2011

Related U.S. Application Data

(63) Continuation of application No. 11/019,865, filed on Dec. 23, 2004, now Pat. No. 8,039,508, which is a continuation of application No. 10/154,494, filed on May 23, 2002, now abandoned.

(30) Foreign Application Priority Data

Jun. 6, 2001  (EP) .................................. 01113793

(51) Int. Cl.
*A61K 9/46* (2006.01)
*A61K 9/20* (2006.01)
*A61K 9/48* (2006.01)
*A61K 9/00* (2006.01)
*A61K 31/335* (2006.01)
*A61K 47/00* (2006.01)

(52) U.S. Cl. ........ 424/466; 424/464; 424/451; 424/400; 514/449; 514/777

(58) Field of Classification Search .................. 514/449, 514/777; 424/400, 451, 464, 466
See application file for complete search history.

(56) References Cited

U.S. PATENT DOCUMENTS

| | | | |
|---|---|---|---|
| 4,148,893 A | 4/1979 | Smith | 424/195 |
| 4,598,089 A | 7/1986 | Hadvary et al. | 514/449 |
| 5,447,953 A | 9/1995 | Isler et al. | 514/449 |
| 5,908,697 A | 6/1999 | Roux et al. | 428/402.2 |
| 6,004,996 A | 12/1999 | Shah et al. | 514/449 |
| 6,030,953 A | 2/2000 | Bailly et al. | 514/25 |
| 6,358,522 B1 | 3/2002 | Hug et al. | 424/441 |

(Continued)

FOREIGN PATENT DOCUMENTS

DE    1 965 133    7/1971

(Continued)

OTHER PUBLICATIONS

C. C. Akoh. *Food Technology*, 52(3): 47-53 (1998).

(Continued)

*Primary Examiner* — Shengjun Wang
(74) *Attorney, Agent, or Firm* — George W. Johnston; John P. Parise (57) ABSTRACT

Pharmaceutical compositions that contain a lipase inhibitor having a melting point ≧37° C., a sucrose fatty acid ester wherein the sucrose fatty acid ester is a mono-, di-, tri- or tetra-ester, and optionally one or more pharmaceutically acceptable excipients, are useful for treatment of obesity.

19 Claims, 3 Drawing Sheets

U.S. PATENT DOCUMENTS

| | | | |
|---|---|---|---|
| 6,534,087 B2 | 3/2003 | Busson et al. | 424/464 |
| 8,039,508 B2 * | 10/2011 | Maeder et al. | 514/449 |
| 2002/0042395 A1 | 4/2002 | Hadvary et al. | 514/58 |
| 2003/0181512 A1 | 9/2003 | de Schmidt et al. | 514/449 |

FOREIGN PATENT DOCUMENTS

| | | |
|---|---|---|
| EP | 185 359 | 6/1986 |
| EP | 189 577 | 8/1986 |
| EP | 0 230 332 | 7/1987 |
| EP | 443 449 | 8/1991 |
| EP | 524 495 | 1/1993 |
| EP | 271 963 | 6/1998 |
| JP | 3112473 | 5/1992 |
| WO | WO 92/17077 | 10/1992 |
| WO | WO 98/34607 | 8/1998 |
| WO | WO 99/34786 | 7/1999 |
| WO | WO 00/09122 | 2/2000 |
| WO | WO 00/09123 | 2/2000 |
| WO | WO 00/25598 | 5/2000 |
| WO | WO 00/40569 | 7/2000 |
| WO | WO 01/19340 | 3/2001 |
| WO | WO 01/19378 | 3/2001 |
| WO | WO 01/32616 | 5/2001 |
| WO | WO 01/32669 | 5/2001 |
| WO | WO 01/32670 | 5/2001 |

OTHER PUBLICATIONS

Allen, et al., *J. Surfactants Deterg.*, 2: 383-390 (1999).
Garti, et al. *J. Mol. Liq.*, 80: 253-296 (1999).
Lookene, et al. *Eur. J. Biochem.*, 222: 395-403 (1994).
Mitsubishi-Kagaku Food Corporation, Guide to similar grade of sucrose ester (2002).
Mutoh, et al. *J. Antibiotics*, 47: 1369-1375 (1994).

* cited by examiner

LIPASE INHIBITING COMPOSITION

BACKGROUND OF THE INVENTION

This application is a continuation of Ser. No. 11/019,865, filed Dec. 23, 2004 now U.S. Pat. No. 8,039,508, (allowed), which is a continuation of Ser. No. 10/154,494, filed May 23, 2002, (abandoned).

FIELD

The present invention relates to lipase inhibiting compositions having reduced food dependency and decreased formation of free oil.

DESCRIPTION

Lipase inhibitors are well known in the art and include lipstatin and orlistat. The latter is also known as tetrahydrolipstatin or THL and is derived from a natural product excreted by *Streptomyces toxytricini*. This class of compounds was found to exhibit in vitro as well as in vivo activity against various lipases, such as lingual lipase, pancreatic lipase, gastric lipase, and carboxylester lipase. Its use for the control or prevention of obesity and hyperlipidemia is described, for instance, in U.S. Pat. No. 4,598,089.

Orlistat is currently administered at doses of 120 mg per meal and dosing is independent of the body mass of the human subject. Orlistat acts locally in the gastrointestinal ("GI") tract and prevents lipase from digesting triglycerides and thus inhibits the formation of absorbable lipid degradation products. For this reason, systemic availability of the lipase inhibitors is not required and, instead, local residence in the GI tract is the preferred mode of delivery.

Lipase inhibitor compositions currently administered inhibit around 30% of fat absorption after consumption of a mixed meal; increasing the concentrations of lipase inhibitors in the pharmaceutical composition does not increase its clinical efficacy and/or potency while the intensity of local side effects increases.

Anal leakage of oil (oily spotting) is an adverse effect, which is occasionally observed by patients treated with lipase inhibitors. This phenomenon reflects physical separation of some liquid unabsorbed dietary fat from the bulk of solids in the lower large intestine.

U.S. Pat. No. 5,447,953 discloses that by combining a lipase inhibitor with substantial amounts of water insoluble crude fibers, the inhibiting effect on fat absorption can be increased. Patent publication WO 00/09123 discloses that by combining a lipase inhibitor such as orlistat with low amounts of chitosan or a derivative or a salt thereof, the phenomenon of anal leakage of oil can be reduced.

International Patent Application WO 01/19378 discloses solid lipid formulations for lipase inhibitors useful to reduce or prevent fat excretion and unwanted formation of free oil. It has been found that a higher efficacy (high fat excretion) can be combined with a lowering of unwanted side effects, e.g. free oil. Recently it has been recognized that the efficacy of lipase inhibitors may depend strongly on the kind of the ingested food. A high efficacy have been found with meals composed of French fries, sausages and hamburgers, while lower efficacy was observed for cheese and other dairy products. Strong food dependency of the formulation efficacy is an unwanted phenomena, because either the formulation is overdosed in susceptible diets (with the consequence of free oil formation) or not active in less susceptible diets. Therefore, the decrease of the food dependency is a prerequisite to realize scenarios with a low dosage of the inhibitor, a high efficacy and less fewer side effects.

Surprisingly, the subject inventors discovered that a certain sucrose fatty acid ester subgroup can increase the activities of lipase inhibitors, decrease the food dependency and decreasing the formation of free oil.

SUMMARY OF THE INVENTION

The subject invention provides a pharmaceutical composition comprising a lipase inhibitor having a melting point $\geq 37°$ C., a sucrose fatty acid ester wherein the sucrose fatty acid ester is a mono-, di-, tri- or tetra-ester, and one or more pharmaceutically acceptable excipients.

DETAILED DESCRIPTION OF THE PREFERRED EMBODIMENTS

The subject invention will now be described in terms of its preferred embodiments. These embodiments are set forth to aid in understanding the subject invention but are not to be construed as limiting.

The present invention relates to a pharmaceutical composition comprising a lipase inhibitor, preferably orlistat, having a melting point $\geq 37°$ C., a sucrose fatty acid ester wherein the sucrose fatty acid ester is a mono-, di-, tri- or tetra-ester, and optionally one or more pharmaceutically acceptable excipients.

Sucrose fatty acid esters are nonionic surfactants consisting of sucrose as hydrophilic moiety and one or more fatty acid moieties as lipophilic group(s). They are manufactured from purified sugar and vegetable oils. As sucrose has a total of 8 hydroxyl groups, compounds ranging from sucrose mono to octa fatty acid esters can be produced. The following formula shows as an example the chemical structure of sucrose monostearate:

The term "sucrose fatty acid ester" comprises one single sucrose fatty acid ester as well as a mixture of two or more sucrose ester fatty acids as defined below. In a preferred embodiment of the present invention the substitution degree of sucrose ester varies between 1 and 4; e.g. mono-, di-, tri-, tetra-ester of fatty acids with sucrose. The term includes pure sucroseesters as well as mixtures of sucroseesters, wherein the sucroseester might be esterified by different fatty acids and might have several substitution degrees, e.g. mono-, di-, tri- or tetra-substituted.

Sucrose fatty acid ester and mixtures thereof and there preparation are known in the art and commercially available [Mitsubishi-Kagaku Foods Corp., Montello Inc., Multi-Kem Corp., etc.; see also Garti et al., Sucrose Ester Microemulsions. *J Mol. Liq.*, 80 (2,3), 253-296 (1999); and Allen et al., Carbohydrate-Alkyl Ester Derivatives as Biosurfactants, *J. Surfactants Deterg.*, 2 (3), 383-390 (1999)].

The term "lipase inhibitor" refers to compounds which are capable of inhibiting the action of lipases, for example gastric and pancreatic lipases. For example, orlistat and lipstatin as described in U.S. Pat. No. 4,598,089 are potent inhibitors of lipases. Lipstatin is a natural product of microbial origin, and orlistat is the result of a hydrogenation of lipstatin. Other lipase inhibitors include a class of compounds commonly referred to as panclicins. Panclicins are analogues of orlistat [Mutoh et al., *J. Antibiot.*, 47 (12), 1369-1375 (1994)]. The term "lipase inhibitor" refers also to synthetic lipase inhibitors for example described in International Patent Application WO 99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. In addition, the term "lipase inhibitor" also refers to 2-oxy-4H-3,1-benzoxazin-4-ones which have been described in International Patent Application WO00/40569 (Alizyme Therapeutics Ltd.), e.g. 2-decyloxy-6-methyl-4H-3,1-benzoxazin-4-one, 6-methyl-2-tetradecyloxy-4H-3,1-benzoxazin-4-one, and 2-hexadecyloxy-6-methyl-4H-3,1-benzoxazin-4-one and other oxetanones described for example in International Patent Applications WO 01/32616, WO01/32669 and WO 01/32670. Most preferably, the term "lipase inhibitor" refers to orlistat.

In German Patent DE 1965133 (Merck) some poly(styrene) derived polymers are described which exhibit direct lipase inhibition next to bile acid and triglyceride binding properties.

Orlistat is a known compound (formula I) useful for the control or prevention of obesity and hyperlipidemia.

(I)

See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122, WO 00/09123, WO 01/19340 and WO 01/19378. Additional processes for the preparation of orlistat are disclosed in European Patent Applications Publication Nos. 185,359, 189,577, 443,449, and 524,495.

In a preferred embodiment of the present invention, the sucroseester molecules are mono-, di- or tri-ester. More preferably, the sucrose ester molecules are a mono- or di-ester and most preferably the sucrose ester are a mono-ester.

In a di-, tri or tetra-ester the fatty acid moieties may be identical or different (e.g. sucrosepalmitostearate), preferably identical.

The preferred ratio (w/w) between the lipase inhibitor and the sucrose fatty acid ester is as follows: The composition may comprise 0.05 mg to 20 mg sucrose fatty acid ester per 1 mg lipase inhibitor, preferably 0.1 mg to 10 mg sucrose fatty acid ester per 1 mg lipase inhibitor, more preferably 0.1 to 2 mg sucrose fatty acid ester per 1 mg lipase inhibitor and most preferably 0.15 to 1 mg sucrose fatty acid ester per 1 mg lipase inhibitor.

Preferably, the lipase inhibitor is a lipophilic compound. Most preferably, the lipase inhibitor is orlistat.

In a further preferred embodiment of the present invention, the fatty acid moiety of the sucrose fatty acid ester is a $C_8$ to $C_{24}$ saturated or partially non-saturated fatty acid. Preferably, the fatty acid moiety of the sucrose fatty acid ester is a $C_{12}$ to $C_{18}$ saturated fatty acid, e.g. sucroselaurate, sucrosemyristate, sucrosepalmitate, sucrosestearate, sucrosearachidonate and sucrosebehanate, preferably sucroselaurate, sucrosemyristate, sucrosepalmitate, sucrosestearate, more preferably sucrosepalmitate or sucrosestearate. In a further preferred embodiment of the invention the fatty acid of the sucrose ester may be selected from $C_8$ to $C_{24}$, preferably a $C_{12}$ to $C_{18}$, mono-or polyunsaturated fatty acids, e.g. selected from the group consisting of palmitoleic acid, oleic acid, elaidic acid, erucic acid, linoleic acid, gamma-linolenic acid, alpha-linolenic acid and arachidonic acid, most preferably oleic acid, i.e. sucrose fatty acid esters may be sucroseoleate.

The fatty acid moieties in a di-, tri-, or tetra-sucrose fatty acid ester may be a mixture of two or more fatty acid, e.g. sucrosepalmitostearate.

For lipase inhibitors as described above, e.g. orlistat, preferred compositions comprise 10 to 240 mg, more preferably 30 to 120 mg, e.g. 30, 40, 60, 80, 100, or 120 g. Especially preferred compositions comprise 60 to 120 mg orlistat and 20 mg to 100 mg sucrose fatty acid ester.

For example a composition as defined above may comprise 120 mg orlistat and 60 mg sucrose ester or 120 mg orlistat and 30 mg sucrose fatty acid ester. Another composition may comprise 80 to 120 mg orlistat and 10 to 40 mg sucrose fatty acid ester or 20 to 60 mg orlistat and 5 to 15 mg sucrose fatty acid ester.

Each dosage unit of the above pharmaceutical compositions can obtain the daily doses of the pharmaceutically active compound or may contain a fraction of the daily dose, such as one-third of the doses. Alternatively, each dosage unit may contain the entire dose of one of the compounds, and a fraction of the dose of the other compound. In such case the patient would daily take one of the combination dosage units, and one or more units containing only the other compound.

Orlistat is preferably orally administered from 30 to 800 mg per day in divided doses two to three times per day (see above). Other preferred daily doses may range between 120 to 360 mg, more preferred are daily doses between 180 to 270 mg and most preferably are 180 mg. Daily doses are, preferably divided and administrated twice or, particularly, three times per day. Generally, it is preferred that the lipase inhibitor has to be administered within about one or two hours of ingestion of a meal containing fat. Generally, for administering a lipase inhibitor as defined above it is preferred that treatment be administered to a human who has a strong family history of obesity or has obtained a body mass index of 25 or greater.

The compositions of the present invention may be administered to humans in conventional oral compositions, such as, tablets, coated tablets, hard and soft gelatin capsules, emulsions, suspensions, sachets, bars or cracker. Examples of carriers which can be used for tablets, coated tablets, dragees, hard gelatin capsules and sachets are pharmaceutically acceptable excipients like lactose, other sugars and sugar alcohols like sorbitol, mannitol, maltodextrin, or other fillers; surfactants like sodium lauryl sulfate, Brij 96, Tween 80; disintegrants like sodium starch glycolate, maize starch or derivatives thereof; polymers like povidone, crospovidone; lubricants like talc; stearic acid or its salts and the like. Moreover, the pharmaceutical preparations can contain preserving agents, solubilizers, stabilizing agents, wetting agents, binding agents, emulsifying agents, sweetening agents, coloring agents, flavoring agents, salts for varying the osmotic pressure, buffers, coating agents and antioxidants. They can also contain still other therapeutically valuable substances. The formulations may conveniently be presented in unit dosage form and may be prepared by any methods known in the pharmaceutical art.

Especially, the above compositions may comprise one or more pharmaceutically acceptable excipients selected from the group consisting of mannitol, lactose, HPMC, lecthin, talcum, sorbitol, polyvinylpyrrolidone, polyethylenglycol, polysorbate, polyoxethylenstearate, and dimethicon, preferably lactose.

Oral dosage forms are the preferred compositions for use in the present invention and these are the known pharmaceutical forms for such administration, for example tablets, capsules or sachets. The pharmaceutically acceptable excipients (diluents and carriers) are known in the pharmacist's art. Tablets may be formed from a mixture of the active compounds with fillers, for example calcium phosphate; disintegrating agents, for example maize starch, lubricating agents, for example magnesium stearate; binders, for example microcrystalline cellulose or polyvinylpyrrolidone and other optional ingredients known in the art to permit tabletting the mixture by known methods. Similarly, capsules, for example hard or soft gelatin capsules, containing the active compound with or without added excipients, may be prepared by known methods. The contents of the capsule may be formulated using known methods so as to give sustained release of the active compound. For example, the tablets and capsules may conveniently each contain the amounts of a pharmaceutically active compound and a sucrose ester as described above.

The term "pharmaceutically acceptable" as used herein means that the corresponding compounds are acceptable from a toxicity viewpoint.

The oral dosage form may be a chewable tablet comprising 10-240 mg of orlistat, 0.5-1000 mg of sucrose fatty acid ester and further excipients such as maltodextrin, lactose or cellulose, for example 120 mg orlistat, 30 mg sucrosepalmitate e.g. Sucrosepalmitate P1670, 960 mg maltodextrin, 360 mg Cellactose and 15 mg talcum.

In the compositions of the present invention the active compounds may, if desired, be associated with other compatible pharmacologically active ingredients. Optionally vitamin supplements may be administered with the compounds of the present invention.

The invention also refers to a process for preparing a composition as described above, comprising mixing a pharmaceutically active compound thereof with sucrose fatty acid ester and one or more pharmaceutically acceptable diluents and/or carriers.

The invention also provides the use of the above combination of compounds in the manufacture of a medicament for the treatment and prevention of obesity. Additionally, it provides the above compositions for use in the treatment and prevention of obesity.

In addition, the present invention refers to a method of treatment of obesity in a human in need of such treatment which comprises administration to the human of a pharmaceutically active compound as defined above and a sucrose fatty acid ester, and optionally additional pharmaceutical acceptable excipients.

The invention also refers to the use of a composition as defined above for use in the treatment and prevention of obesity.

Another embodiment of the present invention refers to a process for preparing a composition as defined above, comprising mixing a pharmaceutically active compound as defined in claim 1 with sucrose ester, and optionally, more pharmaceutically acceptable diluent and/or carrier.

Further the invention refers to a kit for treatment of obesity, said kit comprising a first component which is a lipase inhibitor and a second component which is sucrose fatty acid ester unit dosage forms.

Another embodiment relates to the use of a composition as defined above in the manufacture of medicaments useful for the treatment and prevention of obesity and to a method of treatment of obesity in a human in need of such treatment which comprises administration to the human of a therapeutically effective amount of a lipase inhibitor and a sucrose ester defined above. The invention also refers to a lipase inhibitor and sucrose ester as defined above for the treatment and prevention of obesity.

The invention will be better understood by reference to the following examples which illustrate but do not limit the invention described herein.

EXAMPLES

All compounds used in the examples are commercially available.

Example 1

Orlistat Transfer Into Oil In Vitro

| Formulation | Transfer in Cream (%) | | Transfer in Oliveoil (%) | |
|---|---|---|---|---|
| | after 10' | after 60' | after 10' | after 60' |
| Xenical | 5 | 10 | 35 | 70 |
| L-1695 | 55 | 65 | 55 | 80 |
| P-1670 | 25 | 45 | 50 | 80 |
| S-1670 | 10 | 25 | 60 | 90 |
| O-1570 | 55 | 65 | 45 | 80 |

Orlistat (4 mg) suspensions stabilized by sucroseesters (2 mg) were transferred into 5 ml of a 10% oil in water emulsion (pH value 4.5; oil components: olive oil and cream respectively). The dispersion underwent end-over end mixing for a desired period of time. The oil phase was separated by cold centrifugation and the orlistat content in the oil phase was determined by HPLC. For comparison, an adequate experiment was also performed with a suspension of XENICAL® brand of orlistat-containing pharmaceutical composition. L-1695, P-1670, S-1670, O-1570 are commercial sucroseesters (Sucroselaurate, Sucrosepalmitate, Sucrosestearate, Sucroseoleate respectively) from Mitsubishi-Kagaku Foods, Japan.

The results indicate that the sucroseester have a higher efficacy of the transfer orlistat transfer into oil compared to XENICAL®. In addition to a general higher transfer efficacy and in contrast to XENICAL®, orlistat is transferred into different kind of oils (cream: emulsified and casein covered oily droplets; olive oil: unprotected oil) at more comparable rates. The high food dependency of orlistat is reflected in the fact, that the transfer after 10 min into olive oil is 7 times more efficient than the transfer into cream. The sucrose ester show less food dependency. Therefore, a dose reduction and decreased side effects can be expected.

Example 2

Tablet Formulation

Chewable tablets of the following composition were made:

| Composition 1 | |
|---|---|
| Orlistat | 120 g |
| Sucrosepalmitate P1670 | 30 g |
| Maltodextrin | 960 g |
| Cellactose | 360 g |
| Talcum | 15 g |

Orlistat, sucrosepalmitate and maltodextrin were homogeneously mixed and 350 g water were added stepwise under continuous mixing.

With the help of a syringe the homogeneous dispersion were spread on a sieve (mesh size 0.5 mm) in tracks. The sieve was put into a vacuum drying oven (Heraeus VT 5050 EK) which was tempered to 25° C. Chamber pressure was lowered to 30 Torr (Leybold Heraeus TRIVAC D8B; COMAT AG DPI 700). After 5 minutes, the development of a foam structure was completed. The foam was dried in vacuum for several hours. Care was taken to control that the temperature of the foam did not exceed 35° C. The resulting foam was desintegrated and sieved in order to achieve a homogenous flowable powder. Cellactose and talcum were added and homogeneously distributed by dry mixing. The resulting composition was tabletted into tablets containing Orlistat 120 mg, Sucrosepalmitate 30 mg, Maltodextrin 960 mg, Cellactose 360 mg, and Talcum 15 mg.

Example 3

Chewable Tablet Formulation

Chewable tablets of the following composition were made:

| Composition 2 | |
|---|---|
| Orlistat | 120 g |
| Sucrosepalmitate P1670 | 240 g |
| Maltodextrin | 750 g |
| Cellactose | 375 g |
| Talcum | 15 g |

The tablets were made by the same procedure as described in Example 2.

Example 4

Chewable Tablet Formulation

Chewable tablets of the following composition were made:

| Composition 3 | |
|---|---|
| Orlistat | 60 g |
| Sucrosepalmitate P1670 | 60 g |
| Maltodextrin | 750 g |
| Cellactose | 375 g |
| Talcum | 15 g |

The tablets were made by the same procedure as described in Example 2.

Example 5

Chewable Tablet Formulation

Chewable tablets of the following composition were made:

| Composition 4 | |
|---|---|
| Orlistat | 60 g |
| Sucrosestearate S1811 | 60 g |
| Maltodextrin | 750 g |
| Cellactose | 375 g |
| Talcum | 15 g |

The tablets were made by the same procedure as described in Example 2.

Example 6

Chewable Tablet Formulation

Chewable tablets of the following composition were made:

| Composition 5 | |
|---|---|
| Orlistat | 60 g |
| Sucrosemyristate M1695 | 60 g |
| Maltodextrin | 750 g |
| Cellactose | 375 g |
| Talcum | 15 g |

The tablets were made by the same procedure as described in Example 2.

Example 7

Chewable Tablet Formulation

Chewable tablets of the following composition were made:

| Composition 6 | |
|---|---|
| Orlistat | 60 g |
| Sucrosestearate S1816 | 60 g |
| Maltodextrin | 750 g |
| Cellactose | 375 g |
| Talcum | 15 g |

The tablets were made by the same procedure as described in Example 2.

Example 8

Pellet Formulation

| Composition 7 | |
|---|---|
| Orlistat | 240 g |
| Sucrosepalmitate P1670 | 60 g |
| Avicel PH-105 | 35 g |
| Sodium starch glycolate | 60 g |
| Povidone K30 | 30 g |

The ingredients are dry mixed together in a high speed mixer Diosna P50). 240 g water are added stepwise and the mixing process is continued for about 5 minutes. An extruder is fed with this material (NICA lab E-140; screen 0.8 mm mesh size, thickness 1.0 mm, screen surrounded by cooling device). The material is extruded to spaghettis of appropriate length. The temperature of the extrudate does not exceed 35° C. The extrudate is transferred to a spheronizer ((NICA lab S320) and spheronized for 0.5 to 3 minutes at 700 rpm. The wet pellets are dried in a fluidized bed dryer (Aeromatic, MP-1) at a temperature of below 35° C. The dried pellets are sieved with sieve inserts of 0.5 and 1.25 mm mesh size, and under- and oversize fractions are discarded. The pellets are filled into a sachet at doses of 106 mg (corresponding to 60 mg orlistat).

Example 9

Capsule Formulation

The above pellets are filled into Gelatin capsules size I at a dosage of 106 mg (corresponding to 60 mg orlistat).

Example 10

Tablet Formulation

Magnesium stearate is added to the pellets described in Example 8 at a level of 1% (w/w) and homogeneously distributed by appropriate mixing. The mixture is compressed into 107 mg tablets which correspond to 60 mg orlistat.

Example 11

In Vitro Efficacy

TABLE

Reduced food-dependent efficacy of sucrose ester based orlistat formulations in an in vitro lipase inhibition assay with accessible and resistant fat.

| | Hamburger/ French fries $IC_{50}$ (µg/ml) | Cream $IC_{50}$ (µg/ml) | $\frac{IC_{50, Cream}}{IC_{50, Hamb.}}$ |
|---|---|---|---|
| Xenical-Dispersion | 2.5 | 46 | 5% |
| Dispersion from Example 2 (30 mg Sucrosepalmitate) | 2.8 | 9.0 | 31% |
| Dispersion from Example 3 (240 mg Sucrosepalmitate) | 1.9 | 5.5 | 34% |

Xenical ® pellets and Tablets from Example 2 and Example 3 were investigated. Water was added to a dispersed tablet to yield a orlistat concentration of 6.64 mg/ml. The sample was stirred for 15 min and a geometric dilution series was prepared. An aliquot from each dilution step was mixed with substrate and assessed for lipase inhibition. The final emulsion contained 2.5% (w/v) fat and 10 mg/ml USP pancreatin.

The in vitro lipase test mimics the gastro-intestinal fat digestion and assesses formulation dependent inhibition of lipolysis. In this test lipase substrate (cream and grained hamburger/french fries, representing resistant and accessible fat, respectively) is preincubated with a THL-formulation under simulated gastric conditions (i. e. at pH 4.5 in the presence of 20% human gastric fluid). During this preincubation, the formulation can load fat droplets with THL. Lipolysis is then started by adding artificial intestinal fluid, containing bile salts, phospholipids and hydrolytic enzymes (pancreatin). After one hour organic solvent is added to stop the reaction and free fatty acids are quantified. The dose-response curve is dependent on the formulation as well as on the type of substrate employed.

The IC50 value is the concentration which inhibits triglyceride cleavage by 50%. A high food dependency was observed for Xenical, the IC50 increased by a factor of 20. The in vitro food dependency of the sucrose ester based formulations was about 6-times less compared to Xenical®.

Example 12

Efficacy In Vivo

The 120 mg Orlistat tablet formulations described in Example 2 (30 mg Sucrosepalmitate) and Example 3 (240 mg Sucrosepalmitate), and Xenical® were tested on human volunteers by means of a double-meal test, which is composed of accessible fat (Lunch: Hamburger, French fries and a less accessible fat (Dinner: cheese meal). The nonabsorbed fat was determined after Bligh & Dyer [Bligh et al., Can. J. Biochem. Physiol., 37:911 (1959)].

The results indicate (FIG. 1) that the sucrose ester based formulations show an approximate 1.7 times higher efficacy formulation with 240 mg SUCROSEESTER P1670: 67.4 (±5.3%, n=5), formulation with 30 mg SUCROSEESTER P1670 66.6 (±13%, n=4) compared to Xenical® 39.7 (±8.1%, n=5).

Example 13

Food Dependency In Vivo

Figure 2:
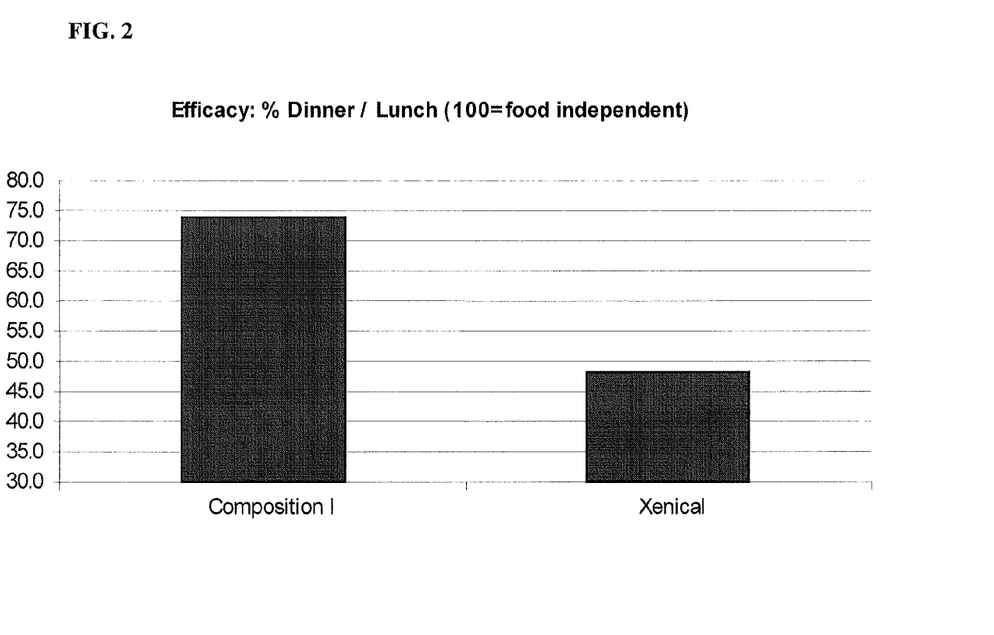
FIG. 2 is a bar graph that indicates the efficacy of Xenical in the less accessible meal was only 48.4% compared to the accessible, while the sucrose ester formulation 30 MG SUCROSEESTER P1670 reached 73.9% (double meal test in human volunteers).

Fatty acid specific analysis of stool permits selective determination of fat uptake of the lunch and dinner meal respectively. The results indicate (FIG. 2) that the efficacy of Xenical® in the less accessible meal was only 48.4% compared to the accessible, while the sucrose ester formulation 30 mg SUCROSEESTER P1670 reached 73.9%. It can be concluded from these data that the food dependency of orlistat can be substantially minimized by sucrose ester based formulations.

Example 14

Side Effect In Vitro Studies

Among various other strategies to control anal leakage, the generation of stable dietary fat emulsion in the colon is of high importance. Therefore, the emulsification properties of sucrose esters covering a wide range of hydrophile-lipophile-balance (HLB) values were investigated using a centrifugal method. This in vitro method allowed both concentration and pH-depended emulsion stabilities to examine and thus to select the sucrose esters of highest potential to control side-effects. The results of the concentration depended emulsion stability studies are listed in Tables 1-3.

TABLE 1

Stability of Surfhope SE Pharma D-1815 test emulsions at various concentrations c and centrifugation times t.

| | Emulsion Stability Surfhope SE Pharma D-1815 t/min | | | | | |
|---|---|---|---|---|---|---|
| c (% w/w) | 10 | 70 | 100 | 160 | 220 | 300 |
| 0.01 | low* | low | low | low | low | low |
| 0.1 | high | medium | medium | medium | medium | medium |
| 0.5 | high | medium | medium | medium | medium | medium |
| 1.0 | high | medium | medium | medium | medium | medium |
| 1.5 | high | medium | medium | medium | medium | medium |
| 2.0 | high | medium | medium | medium | medium | medium |

*low: oil and water form two distinct clearly separated phases; medium: emulsion partly broken;
high: no indications of coalescence, optically non-transparent, stable emulsion

TABLE 2

Stability of Surfhope SE Pharma D-1811 test emulsions at various concentrations c and centrifugation times t.

| | Emulsion Stability Surfhope SE Pharma D-1811 t/min | | | | | |
|---|---|---|---|---|---|---|
| c (% w/w) | 10 | 70 | 100 | 160 | 220 | 300 |
| 0.01 | low* | low | low | low | low | low |
| 0.1 | high | high | medium | medium | medium | medium |
| 0.5 | high | high | medium | medium | medium | medium |
| 1.0 | high | high | high | medium | medium | medium |
| 1.5 | high | high | high | medium | medium | medium |
| 2.0 | high | high | high | high | high | high |

*low: oil and water form two distinct clearly separated phases; medium: emulsion partly broken;
high: no indications of coalescence, optically non-transparent, stable emulsion

TABLE 3

Stability of Surfhope SE Pharma D-1805 test emulsions at various concentrations c and centrifugation times t.

| | Emulsion Stability Surfhope SE Pharma D-1805 t/min | | | | | |
|---|---|---|---|---|---|---|
| c (% w/w) | 10 | 70 | 100 | 160 | 220 | 300 |
| 0.01 | low* | low | low | low | low | low |
| 0.1 | low | low | low | low | low | low |
| 0.5 | medium | medium | medium | medium | medium | medium |
| 1.0 | medium | medium | medium | medium | medium | medium |
| 1.5 | high | medium | medium | medium | medium | medium |
| 2.0 | high | high | high | medium | medium | medium |

Figure 1:
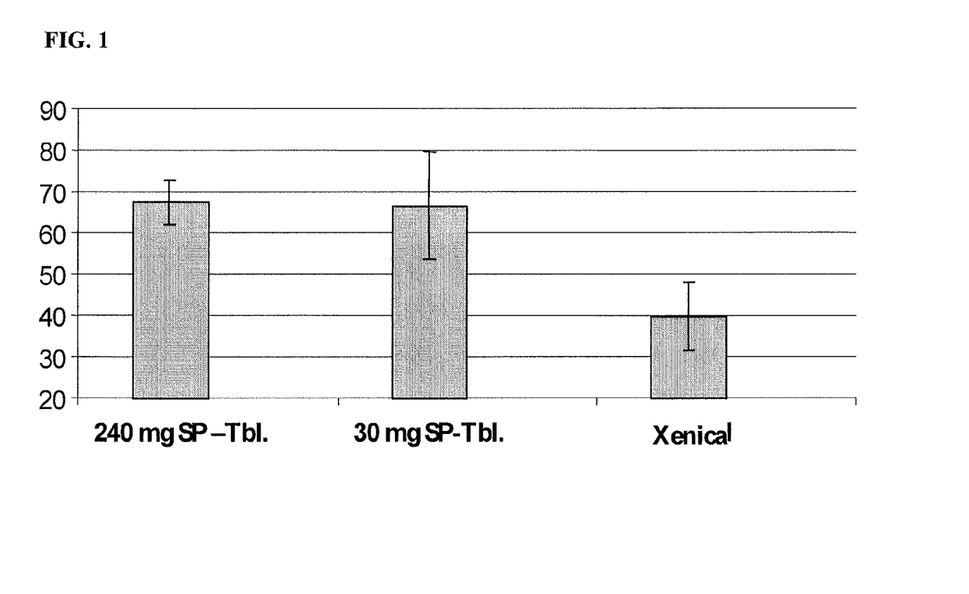
FIG. 1 is a bar graph that indicates that the sucrose ester based formulations show an approximate 1.7 times higher efficacy 240 mg SUCROSEESTER P 1670: 67,4 (±5.3%, n=5), 30 mg SUCROSEESTER P1670 66.6 (±13%, n=4) compared to Xenical 39.7 (±8.1%, n=5) in a double meal test on human volunteers.

*low: oil and water form two distinct clearly separated phases; medium: emulsion partly broken;
high: no indications of coalescence, optically non-transparent, stable emulsion Sucrose esters such as Surfhope SE Pharma D-1811 (Table 2) with a medium HLB value of 11 proofed to be slightly superior in their ability to stabilize an emulsion with respect to Surfhope SE Pharma D-1815 (Table 1) and Surfhope SE Pharma D-1805 (Table 3), respectively. At concentrations of 2.0% (w/w) Surfhope SE Pharma D-1811 revealed stable emulsions without any visual signs of coalescence at centrifugation times up to t=300 min (FIG. 1). Both, Surfhope SE Pharma D-1815 and Surfhope SE Pharma D-1805 showed only slightly less stable emulsion stabilities. In addition, measurements with similarly prepared emulsions stored at room temperature for 1 week without applying any centrifugal force revealed that the conditions generated in the centrifugation experiment correlates to a normal standing period of about 2-3 days, which compares well to the average GI transit time in humans.

Figure 3:
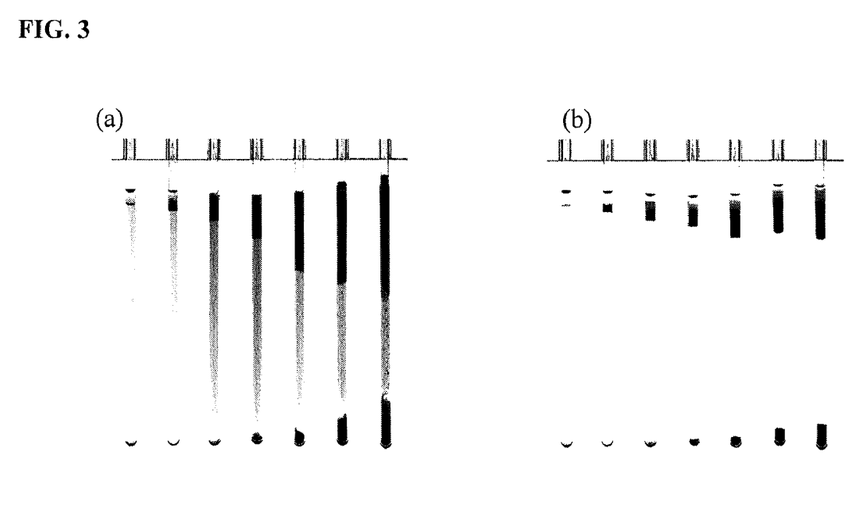
FIG. 3 displays test emulsions of Surfhope SE Pharma D-1811 after centrifugation at 3100 g for t=1 min (a) and t=300 min (b), respectively, The emulsion containing 2.0% (w/w) sucrose ester remains even after a centrifugation time of t=300 min stable (picture (b), right capillary). From left to right: reference (mixture soy oil/buffer); c=0.01%, c=0.1%; c=0.5%; c=1.0%; c=1.5%; c=2.0% (w/w).

FIG. 3 displays test emulsions of Surfhope SE Pharma D-1811 after centrifugation at 3100 g for t=1 min (a) and t=300 min (b), respectively. The emulsion containing 2.0% (w/w) sucrose ester remains even after a centrifugation time of t=300 min stable (picture (b), right capillary). From left to right: reference (mixture soy oil/buffer); c=0.01%, c=0.1%; c=0.5%; c=1.0%; c=1.5%; c=2.0% (w/w).

Similar emulsion stability tests were conducted using combinations of sucrose esters and hydrocolloids (e.g., xanthan gum, gellan gum, carrageenan gum), sphingomyelin, aerosil derivatives, calcium carboxymethylcellulose, chitosan, bentonites, whey protein concentrates, pectins, and poly(vinyl alcohol). Interestingly, these studies showed that 1:1 combinations (w/w) of Surfhope SE Pharma D-1815 and Aerosil 200, carrageenan gum, and whey protein concentrates gave emulsions with clearly better stability than the single compounds alone, due to a yet unknown synergistic mechanism.

In order to investigate emulsion stability at various pH values, test emulsions with a surfactant concentration of c=1.0% w/w covering the range from pH 4 to 9 were prepared (Table 4-7). At pH values >7 all sucrose fatty acid esters investigated showed good emulsification properties. After centrifugation times of 300 min only a small free upper oil phase separated from the optically non-transparent emulsion phase. Sucrose esters with an HLB value below 11 gave only poor emulsification at pH values <7 (Table 5-7). Surprisingly, Surfhope SE Pharma D-1815 with an HLB of 15 gave highly stable emulsions. This clearly indicates that sucrose esters with a rather high HLB value (typically around 15) provide practically pH-independent superior emulsification stabilities.

TABLE 4

Stability of Surfhope SE Pharma D-1815 test emulsions (c = 1.0% w/w) at various pH-values and centrifugation times t.

| | Emulsion Stability Surfhope SE Pharma D-1815 t/min | | | | |
|---|---|---|---|---|---|
| pH | 1 | 30 | 60 | 120 | 300 |
| 4 | high* | high | high | high | high |
| 5 | high | high | high | high | high |
| 6 | high | high | high | high | high |
| 7 | high | high | high | high | medium |
| 8 | high | high | medium | medium | medium |
| 9 | high | high | medium | medium | medium |

*low: oil and water form two distinct clearly separated phases; medium: emulsion partly broken; high: no indications of coalescence, optically non-transparent, stable emulsion

TABLE 5

Stability of Surfhope SE Pharma D-1811 test emulsions (c = 1.0% w/w) at various pH-values and centrifugation times t.

| | Emulsion Stability Surfhope SE Pharma D-1811 t/min | | | | |
|---|---|---|---|---|---|
| pH | 1 | 30 | 60 | 120 | 300 |
| 4 | high* | medium | medium | medium | low |
| 5 | high | medium | medium | medium | low |
| 6 | high | high | medium | medium | medium |
| 7 | high | high | medium | medium | medium |
| 8 | high | high | high | high | medium |
| 9 | high | high | high | high | medium |

*low: oil and water form two distinct clearly separated phases; medium: emulsion partly broken; high: no indications of coalescence, optically non-transparent, stable emulsion

TABLE 6

Stability of Surfhope SE Pharma D-1807 test emulsions (c = 1.0% w/w) at various pH-values and centrifugation times t.

| | Emulsion Stability Surfhope SE Pharma D-1807 t/min | | | | |
|---|---|---|---|---|---|
| pH | 1 | 30 | 60 | 120 | 300 |
| 4 | high* | medium | medium | medium | low |
| 5 | high | medium | medium | medium | low |
| 6 | high | high | medium | medium | low |
| 7 | high | high | high | medium | medium |
| 8 | high | high | high | high | medium |
| 9 | high | high | high | high | medium |

*low: oil and water form two distinct clearly separated phases; medium: emulsion partly broken; high: no indications of coalescence, optically non-transparent, stable emulsion

TABLE 7

Stability of Surfhope SE Pharma D-1805 test emulsions (c = 1.0% w/w) at various pH-values and centrifugation times t.

| | Emulsion Stability Surfhope SE Pharma D-1805 t/min | | | | |
|---|---|---|---|---|---|
| pH | 1 | 30 | 60 | 120 | 300 |
| 4 | low* | low | low | low | low |
| 5 | medium | medium | low | low | low |
| 6 | medium | medium | medium | medium | medium |
| 7 | high | high | medium | medium | medium |
| 8 | high | high | high | high | high |
| 9 | high | high | high | high | high |

Figure 4:
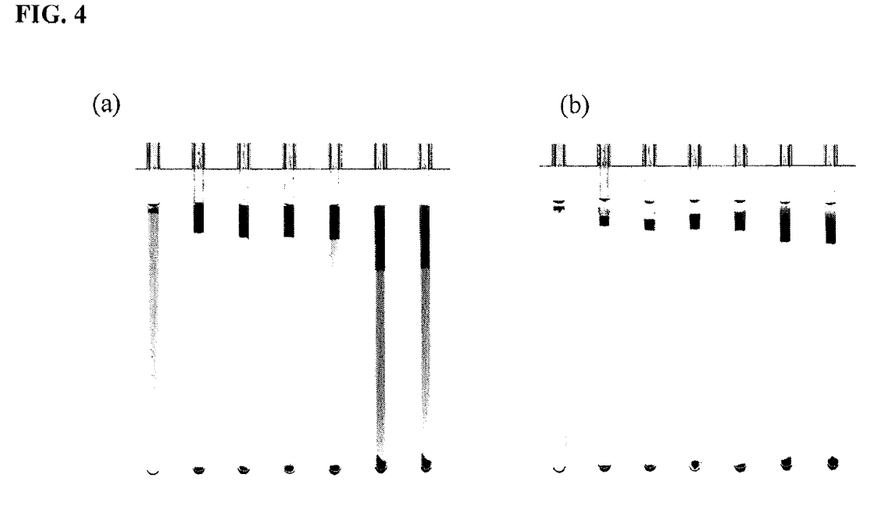
FIG. 4 shows test emulsions of Surfhope SE Pharma D-1811 after centrifugation at 3100 g for t=1 min (a) and t=300 min (b), respectively. The emulsions are stabilized with 1.0% (w/w) sucrose ester at different pH values, Whereas emulsions at pH$\leq$7 clearly show phase separation after centrifugation for t=300 min, emulsions at pH>7 noticeably revealed less free oil.

*low: oil and water form two distinct clearly separated phases; medium: emulsion partly broken; high: no indications of coalescence, optically non-transparent, stable emulsion FIG. 4 shows test emulsions of Surfhope SE Pharma D-1811 after centrifugation at 3100 g for t=1 min (a) and t=300 min (b), respectively. The emulsions are stabilized with 1.0% (w/w) sucrose ester at different pH values. Whereas emulsions at pH $\leq 7$ clearly show phase separation after centrifugation for t=300 min, emulsions at pH >7 noticeably revealed less free oil. From left to right: reference (mixture soy oil/buffer) at pH=7; pH=4, pH=5; pH=6; pH=7; pH=8; pH=9.

In contrast, Sucrose Fatty Acid Ester S-370F revealed very bad emulsification properties. Due to the high hydrophobicity of the compound solubility in the continuous aqueous phase was very low. However, the compound is very easily soluble in soy bean oil resulting in a significant increase in oil viscosity.

Example 15

Side Effect In Vivo Studies

An in vivo mouse model was developed to investigate the ability of sucrose esters to reduce the free oil formation after orlistat treatment. Orlistat was mixed with butter and added to the feed. The concentration of orlistat administered to the mice was 150 µmol orlistat/kg body weight. The experiment is based on the observation that mice under a high fat diet treated with orlistat or other lipase inhibitors distribute the excreted free oil over their furs while grooming (United States patent, U.S. Pat. No. 5,431,949). A variety of sucrose esters as mentioned above were examined for their ability to reduce or eliminate the production of free oil. The results of these studies are summarized in FIG. 5.

Figure 5:
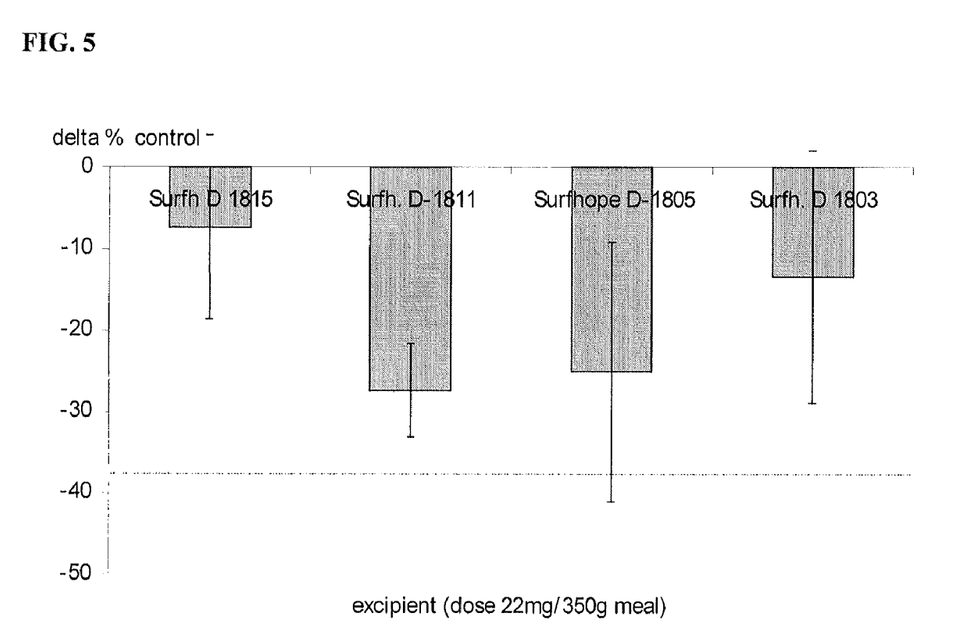
FIG. 5 is a bar graph demonstrating the ability of certain sucrose esters to reduce production of free oil.

In this representation, the excretion of free oil by a control group which received Orlistat but no gastro-intestinal side effect controlling agent was taken as background level and arbitrarily set to zero. Any improvements in free oil production are given as minus per cent value relative to the background. These experiments revealed that sucrose esters such as Surfhope D-1811 or Surfhope D-1805 with a medium HLB value show the highest relative reduction in free oily excretion. In contrast, sucrose esters on either end of the HLB scale which are either very hydrophilic (Surfhope D-1815) or very lipophilic (Surfhope D-1803) show less activity.

Example 16

Pellet Formulation Compressed To Chewable Tablet

| Composition 8 | |
|---|---|
| Orlistat | 240 g |
| Sucrosepalmitate P1670 | 60 g |
| Avicel PH-105 | 210 g |
| Sodium starch glycolate | 60 g |
| Povidone K30 | 30 g |
| Stearic acid | 6 g |

The ingredients are dry mixed together in a high speed Aeromatic Fielder GP 1). 240 g water are added stepwise and the mixing process is continued for about 5 minutes. An extruder is fed with this material (NICA extruder; screen 0.8 mm mesh size, thickness 1.0 mm). The material is extruded to spaghettis of appropriate length. The temperature of the extrudate does not exceed 35° C. The extrudate is transferred to a spheronizer ((NICA spheronizer) and spheronized for 0.5 to 5 minutes. The wet pellets are dried in a fluidized bed dryer (Aeromatic, MP-1) at a temperature of below 35° C. The dried pellets are sieved with sieve inserts of 0.5 and 1.25 mm mesh size, and under- and oversize fractions are discarded. Stearic acid is added and homogeneously distributed by dry mixing. The resulting mixture is compressed to chewable tablets containing orlistat 120 mg, sucrosepalmitate 30 mg, Avicel 105 mg, sodium starch glycolate 30 mg, povidone 15 mg and stearic acid 3 mg.

Example 17

Two layer chewable tablet

| Composition 9 | |
|---|---|
| a) Orlistat | 240 g |
| b) Sucrosepalmitate P1670 | 60 g |
| c) Avicel PH-105 | 210 g |
| d) Sodium starch glycolate | 60 g |
| e) Povidone K30 | 30 g |
| f) Stearic acid | 6 g |
| g) Lactose monohydrate (powder) | 1460 g |
| h) Avicel PH 102 | 200 g |
| i) Maize starch 1500 | 100 g |
| k) Sodium starch glycolate | 100 g |
| l) Povidone 90F | 60 g |
| m) Glyceryl benehate | 60 g |
| n) Magnesium Stearate | 20 g |

Layer 1: The ingredients a)-e) are dry mixed together in a high speed Aeromatic Fielder GP 1). 240 g water are added stepwise and the mixing process is continued for about 5 minutes, An extruder is fed with this material (NICA extruder; screen 0.8 mm mesh size, thickness 1.0 mm), The material is extruded to spaghettis of appropriate length. The temperature of the extrudate does not exceed 35° C. The extrudate is transferred to a spheronizer ((NICA spheronizer) and spheronized for 0.5 to 5 minutes. The wet pellets are dried in a fluidized bed dryer (Aeromatic, MP-1) at a temperature of below 35° C. The dried pellets are sieved with sieve inserts of 0.5 and 1.25 mm mesh size, and under- and oversize fractions are discarded. Stearic acid is added and homogeneously distributed by dry mixing. Layer 2: The excipients g)-m) are mixed together in a high speed mixer (Aeromatic Fielder GP 1) for 5 minutes, 400 g water added for granulation. The wet granulate is sieved and dried in a fluidized bed dryer (Aeromatic, MP-1). The dried granulate is sieved, and homogeneously mixed with Magnesium stearate.

The resulting mixtures of layer 1 and 2 are compressed to a two layer tablet (Kilian compressing equipment) containing orlistat 120 mg, sucrosepalmitate 30mg, Avicel 105 mg, sodium starch glycolate 30 mg, povidone 15mg and stearic acid 3 mg in layer 1 and containing Lactose 730 mg, Avicel 100 mg, maize starch 50 mg, sodium starch glycolate 50 mg, povidone 30 mg, glyceryl benehate 30 mg and magnesium stearate 10 mg in the second layer.

Example 18

Fast Disintegrating Chewable Tablet

| Composition 10 | |
|---|---|
| Orlistat | 48 g |
| Sucrosepalmitate P1670 | 12 g |
| Sodium starch glycolate | 48 g |
| PEG 6000 | 72 g |
| Xylit | 122.4 g |
| Mannit pulvis | 122.4 g |
| Myrj 52 | 12 g |
| Plasdone S630 | 24 g |
| Magnesium stearate | 4.8 g |
| Talc | 24 g |

The ingredients (with exception of magnesium stearate and talc) were mixed in a high speed mixer (Aeromatic Fielder GP 1) for 5 minutes. 32 g water was added for granulation. The wet granulate was sieved (Siebschleuder Bergmeier 5.0 mm) and dried in a fluidized bed dryer (Aeromatic Strea) below 37° C. The dry granulate was sieved (Fitzpatrick 1.62 mm), mixed with Magnesium stearate and Talc and compressed to a chewable tablet (Korsch PH 250 tabletting machine).

Example 19

Fast Disintegrating Chewable Tablet

| Composition 11 | |
|---|---|
| Orlistat | 48 g |
| Sucrosepalmitate P1670 | 12 g |
| Sodium starch glycolate | 48 g |
| PEG 6000 | 72 g |
| Xylit | 98.4 g |
| Mannit pulvis | 98.4 g |
| Myrj 52 | 12 g |
| Alginic acid | 32.64 g |
| Plasdone S630 | 24 g |
| Magnesium stearate | 4.8 g |
| Talc | 14.4 g |
| Calcium carbonate | 15.36 g |

The ingredients (with exception of magnesium stearate, talc and calcium carbonate) were mixed in a high speed mixer (Aeromatic Fielder GP 1) for 5 minutes. 30 g water was added for granulation. The wet granulate was sieved (Siebschleuder Bergmeier 5.0 mm) and dried in a fluidized bed dryer (Aeromatic Strea) below 37° C. The dry granulate was sieved (Fitzpatrick 1.62 mm), homogeneously mixed with magnesium stearate, talc and calcium carbonate and compressed to a chewable tablet (Korsch PH 250 tabletting machine).

Upon reading the present specification various alternative embodiments will become obvious to the skilled artisan. These variations are to be considered within the scope and spirit of the subject invention which is only to be limited by the claims that follow and their equivalents.

What is claimed is:
1. A pharmaceutical composition comprising
 (i) orlistat;
 (ii) a sucrose fatty acid ester or a mixture of sucrose fatty acid esters, wherein the sucrose fatty acid ester comprises a sucrose moiety and at least one to four fatty acid moieties, and wherein the fatty acid moiety in the sucrose fatty acid ester or mixture of sucrose fatty acid esters is selected from the group consisting of a saturated or partially non-saturated C8-C24; and wherein the sucrose fatty acid ester or a mixture of sucrose fatty acid esters have an HLB value of about 11 to about 15;

(iii) one or more pharmaceutically acceptable excipients.

2. The composition according to claim 1, wherein the composition comprises 20 to 60 mg orlistat.

3. The composition according to claim 1, wherein the sucrose fatty acid ester or a mixture of sucrose fatty acid esters have an HLB value of about 15.

4. The composition according to claim 1, wherein 0.05 mg to 20 mg sucrose fatty acid ester or mixture of sucrose fatty acid esters is used per 1 mg orlistat.

5. The composition according to claim 1, wherein the sucrose fatty acid ester contains at least two fatty acid moieties.

6. The composition according to claim 5 wherein the two fatty acid moieties are the same or different.

7. The composition according to claim 6 wherein the two fatty acid moieties are the same.

8. The composition according to claim 1, wherein the sucrose moiety in the sucrose fatty acid ester or mixture of sucrose fatty acid esters is about 80% mono esterified.

9. The composition according to claim 1 wherein in the mixture of sucrose fatty acid esters the most prevalent sucrose fatty acid ester in said mixture is a mono ester.

10. The composition according to claim 9, wherein the at least one fatty acid moiety in the sucrose fatty acid ester is palmitic acid.

11. The composition according to claim 1, wherein the at least one fatty acid moiety is selected from the group consisting of palmitic acid, lauric acid, myristic acid and stearic acid.

12. The composition according to claim 1, wherein the sucrose fatty acid ester is sucroselaurate or a mixture of sucrose fatty acid esters containing sucroselaurate.

13. The composition according to claim 1, wherein the sucrose fatty acid ester is sucrosemyristate or a mixture of sucrose fatty acid esters containing sucrosemyristate.

14. The composition according to claim 1, wherein the sucrose fatty acid ester is sucrosepalmitate or a mixture of sucrose fatty acid esters containing sucrosepalmitate.

15. The composition according to claim 1, wherein the sucrose fatty acid ester is sucrosestearate or a mixture of sucrose fatty acid esters containing sucrosestearate.

16. The composition according to claim 1, wherein the composition comprises one or more pharmaceutically acceptable excipients selected from the group consisting of mannitol, lactose, HPMC, talcum, sorbitol, polyvinylpyrrolidone, lecithin, polyethylene glycol, polysorbate, polyoxethylenestearate and dimethicon.

17. The composition according to claim 16, wherein the composition comprises 20 to 60 mg orlistat.

18. The composition according to claim 17, in the form of a tablet, a chewable tablet or capsule for oral administration.

19. The composition according to claim 1 wherein the fatty acid moiety is a C12 to C18 saturated fatty acid.

* * * * *